(12) United States Patent
Brooks et al.

(10) Patent No.: US 8,142,512 B2
(45) Date of Patent: Mar. 27, 2012

(54) INSTRUMENT FOR USE IN A JOINT REPLACEMENT PROCEDURE

(75) Inventors: James Brooks, Leeds (GB); Steven Gowers, Leeds (GB); Jonathan Thompson, Leeds (GB)

(73) Assignee: Depuy International Limited (GB)

(*) Notice: Subject to any disclaimer, the term of this patent is extended or adjusted under 35 U.S.C. 154(b) by 19 days.

(21) Appl. No.: 12/593,564

(22) PCT Filed: Mar. 27, 2008

(86) PCT No.: PCT/GB2008/001055
§ 371 (c)(1),
(2), (4) Date: Feb. 23, 2010

(87) PCT Pub. No.: WO2008/117056
PCT Pub. Date: Oct. 2, 2008

(65) Prior Publication Data
US 2010/0179664 A1 Jul. 15, 2010

(30) Foreign Application Priority Data
Mar. 28, 2007 (GB) .................................. 0705905.8

(51) Int. Cl.
*A61F 2/30* (2006.01)
(52) U.S. Cl. .................. 623/23.4; 623/22.43; 623/22.45
(58) Field of Classification Search .... 623/19.11–19.14, 623/22.11, 22.15–22.18, 23.47–23.48, 23.43–23.45
See application file for complete search history.

(56) References Cited

U.S. PATENT DOCUMENTS

| | | | |
|---|---|---|---|
| 4,865,605 A * | 9/1989 | Dines et al. ................ | 623/19.14 |
| 5,002,581 A | 3/1991 | Paxson | |
| 6,206,884 B1 | 3/2001 | Masini | |
| 6,736,852 B2 * | 5/2004 | Callaway et al. .......... | 623/19.14 |
| 2001/0053935 A1 | 12/2001 | Hartdegen | |
| 2002/0193882 A1 | 12/2002 | Koller | |
| 2005/0197708 A1 | 9/2005 | Stone | |
| 2007/0043446 A1 | 2/2007 | Murray | |

FOREIGN PATENT DOCUMENTS

DE 10056698 A1 5/2002

(Continued)

OTHER PUBLICATIONS

Anapliotis E.; German Patent No. De 10056698 A1; May 16, 2002; English Abstract; Derwent World Patents Index; Dialog® File No. 351 Accession No. 12450172; © 2009 Derwent Information Ltd.

(Continued)

*Primary Examiner* — David Isabella
*Assistant Examiner* — Brian Dukert

(57) ABSTRACT

An instrument for use in a joint replacement procedure comprises a head part which corresponds to the head of an orthopaedic joint component, in which the head part has a bore formed in it, and a connector for connecting the head part to a stem part of the orthopaedic joint component, which is intended for location in the intramedullary cavity of a bone. The connector can be fitted into the bore in the head part in one of a plurality of angular orientations. It comprises a body part and a trigger which can be moved relative to the body part between an unlocked position in which the connector can be moved relative to the head part between different ones of the plurality of angular orientations and a locked position in which the connector is restrained against such movement.

16 Claims, 7 Drawing Sheets

FOREIGN PATENT DOCUMENTS

| | | | |
|---|---|---|---|
| EP | 1013245 | A2 | 6/2000 |
| EP | 1258233 | A1 | 11/2002 |
| FR | 2832625 | A1 | 5/2003 |

OTHER PUBLICATIONS

Bouvet J. C.; French Patent No. FR 2832625 A1; May 30, 2003; English Abstract; Derwent World Patents Index; Dialog® File No. 351 Accession No. 13370728; © 2009 Derwent Information Ltd.

Metasul® LDH® Large Diameter Head with Durom® Acetabular Component Surgical Technique; Product Brochure; 97-1081-002-00 Rev. 1 © 2007, 2008 Zimmer, Inc.; www.zimmer.com.

PCT International Search Report PCT/GB2008/001055 dated Mar. 26, 2008.

PCT Written Opinion PCT/GB2008/001055 dated Jul. 14, 2008.

PCT International Preliminary Examination Report PCT/GB2008/001055 dated Jul. 23, 2009.

UK Search Report GB0705905.8 dated Jul. 5, 2007.

\* cited by examiner

FIG. 1
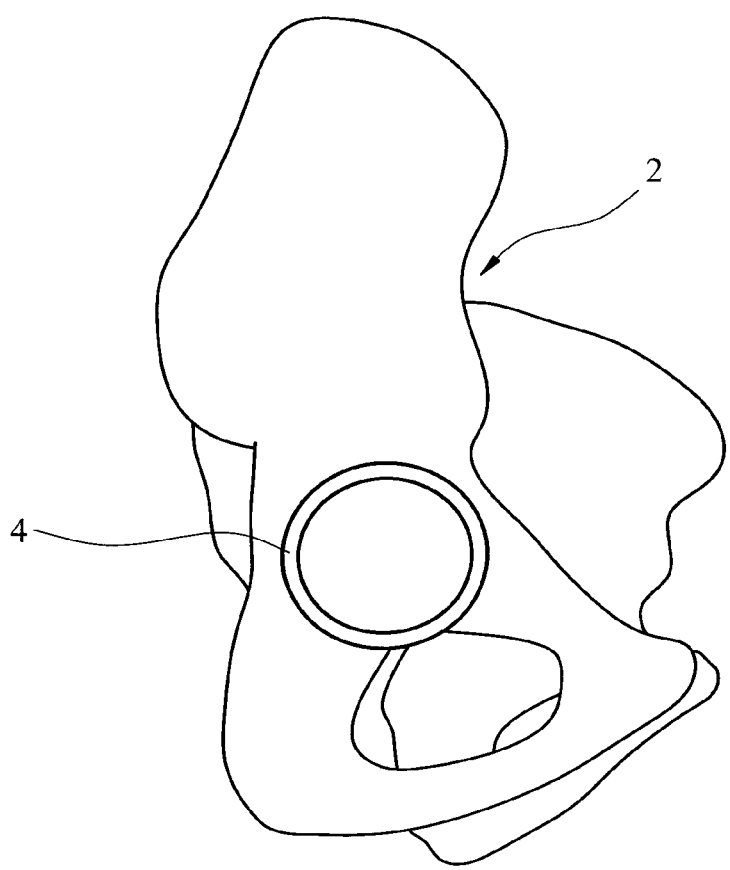
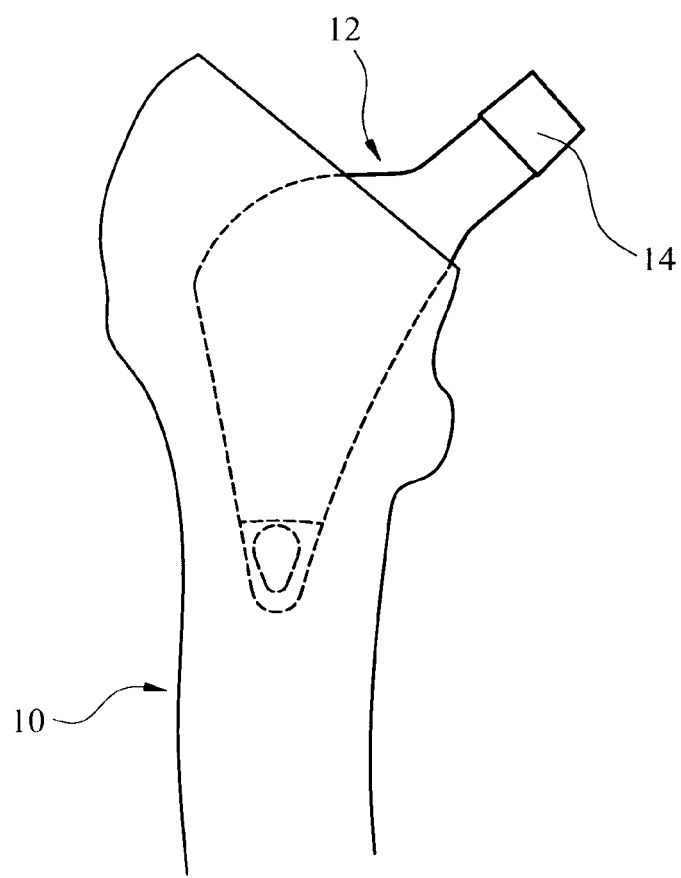
FIG. 2

INSTRUMENT FOR USE IN A JOINT REPLACEMENT PROCEDURE

CROSS REFERENCE TO RELATED APPLICATION

This application is a National Stage 35 U.S.C. 371 of International Patent Application PCT/GB2008/001055 filed on Mar. 27, 2008.

BACKGROUND OF INVENTION

This invention relates to an instrument for use in a joint replacement procedure.

The success of a joint replacement procedure depends in part on the appropriate alignment of the articulating parts of the joint prosthesis. Inappropriate alignment can give rise to post-operative problems, including limited range of motion of the joint, wear of the bearing surfaces which is uneven or excessive, and damage to soft tissue which is associated with the joint.

it is known to construct the humeral component of a shoulder joint prosthesis using a stem part, a head part, and a connector part which can be fitted into a bore in the head part, and has a bore formed in it to receive a spigot on the stem part. Such a device is disclosed in US-A-2005/0197708. The eccentric arrangement of the bore in the head part relative to the axis of the head part, and the eccentric arrangement of the bore in the connector part eccentric relative to the axis of the connector part, allow the distance through which the head part is offset relative to the stem part, and the orientation of that offset, to be adjusted to suit the requirements of a patient. This can facilitate variation of effective arm length, and the extent of retroversion and anteversion.

It is known to use trial implant instruments in a surgical procedure to implant an orthopaedic prosthesis. The use of a trial instrument has the advantage that the configuration of the instrument can be assessed in relation to a mating instrument or implant with a view to selecting the ultimate implant component with the optimum configuration.

US-A-2001/0053935 discloses a trialling system which comprises a plurality of components. It is suitable for use in conjunction with an implant which also comprises a plurality of modular components. The modular trial implant instrument can then enable the configuration of the trial implant instrument to be changed to identify an optimum configuration.

BRIEF SUMMARY OF THE INVENTION

The present invention provides a trial instrument which includes a head part, and a connector by which the head part can be connected to a stem part, in which the connector includes a body part and a trigger which can be moved relative to the body part between an unlocked position in which the connector can be moved relative to the head part between different ones of the plurality of angular orientations and a locked position in which the connector is restrained against such movement.

Accordingly, in one aspect, the invention provides an instrument for use in a joint replacement procedure, which comprises:
a. a head part which corresponds to the head of an orthopaedic joint component, in which the head part has a bore formed in it,
b. a connector for connecting the head part to a stem part of the orthopaedic joint component, which is intended for location in the intramedullary cavity of a bone, in which the connector can be fitted into the bore in the head part in one of a plurality of angular orientations, and in which the connector comprises a body part and a trigger which can be moved relative to the body part between an unlocked position in which the connector can be moved relative to the head part between different ones of the plurality of angular orientations and a locked position in which the connector is restrained against such movement.

The instrument of the invention has the advantage that it enables a trial to be configured conveniently in a particular configuration to enable the suitability of that configuration for implantation to be assessed.

Preferably, the trigger is biassed resiliently towards the locked position. For example, the trigger can be formed from a resiliently deformable material which allows the trigger to be flexed. The trigger can be connected to the body by means of a hinge, and a spring can be used to bias the trigger towards the locked position.

Preferably, the trigger is formed integrally with the connector, for example by machining it, or by a moulding process, such as injection moulding. Moulding processes can conveniently be carried out using materials which are resiliently deformable. A trigger can be formed by a moulding process with a configuration which facilitates deformation, for example such that the trigger has a locally thinner cross-section in region where it is to be deformed.

Preferably, the connector and the head part present a cooperating lug and notch (in which the lug can be received) arrangement which, when the lug is engaged in the notch, resists rotation of the connector within the bore of the head part. The lug and notch arrangement can present a plurality of notches or a plurality of lugs or both. Preferably, the lug and notch arrangement defines at least two angular positions of the connector relative to the head part, more preferably at least four angular positions, for example at least six angular positions. The lug and notch arrangement should preferably define not more than ten angular positions of the connector relative to the head part, for example not more than eight angular positions. The lug can be elongate for example in the form of a rib. The notch can be elongate, for example in the form of a groove.

Preferably, the bore in the head part is located eccentrically relative to the axis of the head part which is defined by the spherical surface thereof.

Preferably, the connector has a first connection feature which comprises one of an inwardly tapered bore and a spigot with a circular cross section, for cooperation with a second connection feature on a stem part comprising the other of an inwardly tapered bore and a spigot such that the spigot can be received in the bore to connect the stem part to the connector part. It will generally be preferred for many applications that the bore is provided in the connector, which can receive a spigot which is provided on the stem part.

Preferably, the first connection feature on the connector is located eccentrically relative to the axis of the connector part.

When features of the connector or of the head part are located eccentrically relative to the axis of that component, the provision of a plurality of angular positions of the connector relative to the head part has the advantage that the configuration of the assembled instrument can be changed, enabling the instrument to be adapted to assess the suitability of a selected configuration of implant component for implantation in a patient. For example, variation of the angular position of the head part axis relative to a stem part by angular adjustment about eccentric axes can enable variations of configuration features of an implant which will affect the effective length of the arm which extends between the axis of the bone on which the stem component is implanted and the head part of the component, and the extent of retroversion and anteversion.

Preferably, the axis of the head part defined by its external surface and the axis of the bore in the head part are approximately parallel. The distance between the axis of the head part defined by its external surface and the axis of the bore in the head part can be at least about 2 mm, for example at least about 5 mm. The distance between the axis of the head part defined by its external surface and the axis of the bore in the head part can be not more than about 10 mm, for example not more than about 8 mm, or not more than about 6 mm.

Preferably, the axis of the connector part defined by its external surface and the axis of the first connection feature are approximately parallel. The distance between the axis of the connector part defined by its external surface and the axis of the first connection feature can be at least about 1 mm, for example at least about 2 mm. The distance between the axis of the connector part defined by its external surface and the axis of the first connection feature can be not more than about 6 mm, for example not more than about 4 mm.

Preferably, the diameter of the bore in the head part at the widest point at which it is contacted by the external surface of the connector part when assembled is not more than about 35 mm, more preferably not more than about 30 mm. Preferably, the diameter of the bore in the head part at the widest point at which it is contacted by the external surface of the connector part when assembled is at least about 10 mm, more preferably at least about 15 mm, for example at least about 20 mm.

Preferably, one of the connector and the head part has a lip formed on it and the other of the connector and the head part has a groove formed in it, in which the lip can fit in the groove when the connector is positioned within the bore in the head part to resist removal of the connector from the bore in the head part. For example, the lip might be provided on the connector and the groove might be provided on the internal surface of the bore in the head part. Preferably, the lip or groove (as the case might be) which is provided on the head part extends continuously around the internal surface of the bore in an annular arrangement. It can be preferred for the lip to be provided on the trigger.

A suitable lip might have a depth measured from its peak to the surface on which the lip is provided) of less than 2.0 mm. A suitable lip might have a depth of at least about 0.75 mm. The lip should be sufficiently deep that it is a secure fit in the groove, and so that the degree of play between the lip and the groove is small.

Generally, the external surface of the head part is part-spherical with an approximately constant radius. Preferably, the radius of the sphere which defines the external surface is at least about 7 mm, more preferably at least about 9 mm, for example at least about 11 mm. Preferably, the radius is not more than about 30 mm, more preferably not more than about 20 mm, for example not more than about 15 mm or about 12 mm.

Preferably, the angle of arc through which the external surface of the head part extends (when the head part is viewed in cross-section on the plane which contains its axis) is at least about 180°, more preferably at least about 190°, for example at least about 200°.

The instrument of the invention can be made from materials which are commonly used in the manufacture of surgical instruments. Examples of such materials include metals and polymers. Examples of suitable metals which might be used in the instrument of the invention include certain stainless steels, as well as alloys of elements such as titanium.

Examples of polymers which might be used in the instrument of the invention include engineering polymers such as polyaryl ether ketones, polyetherether ketones, certain polyamides and polyesters, polyolefins such as certain polyethylenes and polypropylenes, and so on. The properties of the polymer can be adapted to suit particular requirements by addition of a filler, especially a particulate filler.

It can be preferred for the parts of the instrument of the invention to be coloured. It is an advantage of polymeric materials in the present invention that they can be coloured by addition of an appropriate filler or other dye to the polymer composition during manufacture of the parts.

The head part and the connector can be formed from different materials. However, it will generally be preferred for the head part and the connector to be formed from the same material, possibly with some variations such as in terms of colour.

Preferably, the instrument of the invention includes a stem part which corresponds to the stem of an orthopaedic joint component. The stem part can itself provide the connector and engage the head part directly. The stem part and the connector can be provided as separate parts. When the stem part and the connector are provided as separate parts, the stem part can have a connection feature enabling it to be connected to the connector. The connection between the stem part and the connector can be provided, by means of appropriately matched taper surfaces. For example, the stem part can have a tapered spigot, and the connector can have a tapered bore formed in it in which the spigot can be received. A spigot on the stem part might have one of a lug and a notch, and the connector might have the other of a lug and a notch, where the lug can be received in the notch to provide positive engagement between the stem part and the connector.

It can be appropriate for the instrument of the invention to be used in a hip joint replacement procedure, in which case the instrument can include a stem part which can be fitted into the intramedullary cavity of a patients femur. The head part can be arranged to articulate with a cup component which can be placed, in the patient's acetabulum. The instrument of the invention to be used in a shoulder joint replacement procedure, in which case the instrument can include a stem part which can be fitted into the intramedullary cavity of a patient's humerus. The head part can be arranged to articulate with the patient's glenoid or with the glenoid component which can be fitted in the patient's glenoid.

In another aspect, the invention provides an assembly for use in a joint replacement procedure, which comprises an instrument as discussed above, and an orthopaedic joint component which comprises (i) a head part having the shape of a truncated sphere with a convex bearing surface which can engage and articulate with the socket component and an opposite reverse face, the head part having a blind bore with a circular cross section within it located eccentrically relative to the axis of the head part, in which the bore extends into the head part from an opening on the reverse face and is inwardly tapered continuously from the opening towards the blind end thereof, (ii) a stem part having a distal end and a head end, which can be fitted distal end first into a bone cavity, and (iii) a connector part with a circular cross-section which is tapered inwardly along the axis defined by its external surface so that it can be received snugly in the tapered bore in the head part.

BRIEF DESCRIPTION OF THE DRAWINGS

Embodiments of the invention will now be described by way of example with reference to the accompanying drawings, in which:

FIG. 1 is a view of a prepared acetabulum, in which an acetabular cup component has been implanted.

FIG. 2 is a view along the anterior posterior axis of the head of a femur, in which a stem part of a femoral component of a hip joint prosthesis has been implanted.

DETAILED DESCRIPTION OF THE INVENTION

Figure 3:
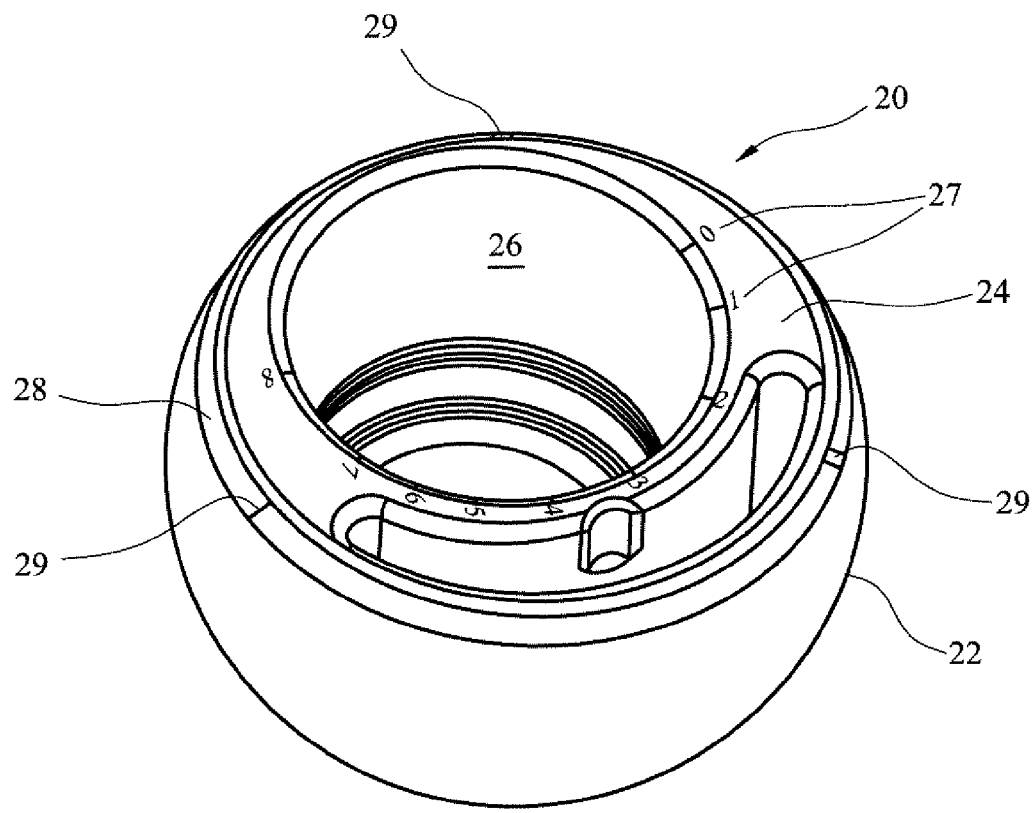
FIG. 3 is a view from below of a head part of a femoral component.

Referring to the drawings, FIG. 1 shows a pelvis 2 which is been reamed to receive the acetabular cup component 4 of a hip joint prosthesis. The acetabular cup component has been implanted using conventional techniques.

FIG. 2 shows the head portion of a femur 10 which has been resected at the base of the femoral neck. The intramedullary cavity has been prepared using conventional techniques (by reaming or broaching or a combination of the two) to receive the stem part 12 of the femoral component of a hip joint prosthesis. The stem part can be fastened in the femur by means of a bone cement material, as is known. The stem part can be fastened in the femur without the use of a bone cement material, as is known.

The stem part has a tapered spigot 14 at its exposed end on which the head part of the femoral component can be fitted. The dimensions of the spigot on the stem part are in line with existing stem parts of femoral components of hip joint prostheses.

FIG. 3 shows the head part 20 of a femoral component of a hip joint prosthesis according to the present invention. The head part has a spherical bearing surface 22 and an opposite reverse face 24. The spherical bearing surface extends through an angle of arc of about 200°. The radius of the bearing surface is 18 mm. The distance from the reverse face of the head part to the point where the polar axis intersects the bearing surface is from 28.25 to 41.8 mm.

A tapered bore 26 is formed in the reverse face 24. The bore has a circular cross-section. At the reverse face, the diameter of the bore is from 24.2 to 28.6 mm. The depth of the bore, measured from the reverse face of the head part to the blind end of the bore, is from 9.0 to 11.5 mm. The angle between the wall of the bore and its axis (which is half of the angle defined by the diametrically opposite walls of the bore) is 5°.

The bore 26 is offset relative to the polar axis (which is the axis extending through the centre of the sphere defined by the bearing surface, perpendicular to the reverse face). The distance between the axis of the bore and the polar axis is from 2 to 4 mm.

The head part has a series of markings 27 on its reverse face. These relate to the distance through which the head part is offset relative to the axis of the stem part when the femoral component is assembled, as discussed below.

The head component has a chamfer surface 28 extending around its periphery where the chamfer and reverse faces come together. The chamfer surface is planar when the component is viewed in cross-section. The angle between the chamfer surface and the polar axis is about 50°. The chamfer surface has three markings 29 at spaced apart points. The markings are distinguishable from one another.

Figure 4:
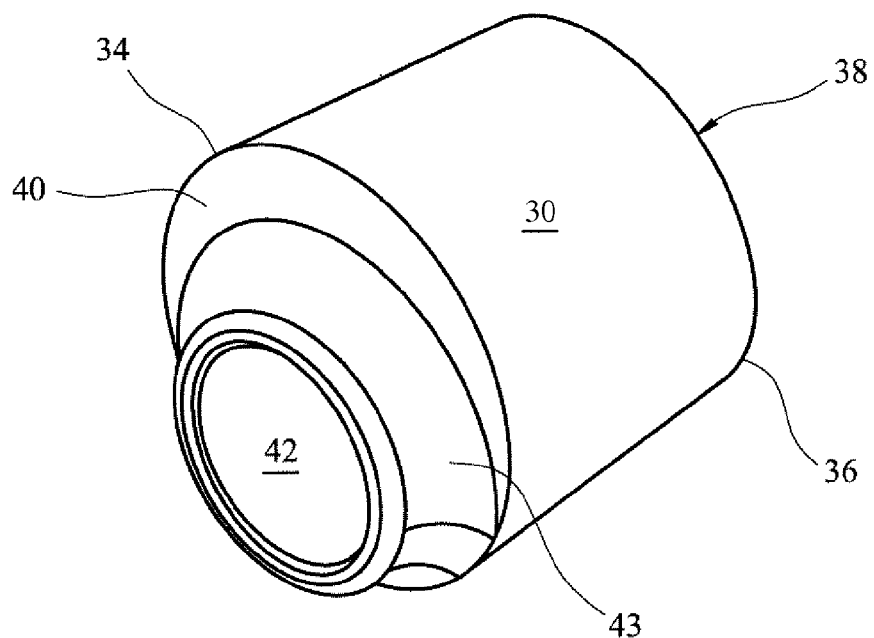
FIG. 4 is an isometric view from below of a connector in place which can be used to connect the head part shown in FIG. 3 to the stem part shown in FIG. 2.

FIG. 4 shows a connector 30 which can be used to connect the head part to the stem part 12 of the femoral component. The connector is circular when viewed from above and is tapered inwardly along the axis defined by its external surface 32. The diameter of the connector at its widest 34 point is from 24.2 to 28.3 mm. The diameter of the connector at its narrowest point 36 is from 22.45 to 20.7 mm. The depth of the connector measured from its top face 38 to its opposite bottom face 40 (not including the skirt which depends from the bottom face is from 19.75 to 22.25 mm. The angle between the wall of the connector and its axis (which is half of the angle defined by the diametrically opposite walls of the connector) is 5°. The connector is therefore a snug fit in the bore 26 in the head part, with the top face 38 located within the bore 26 in the head part, and the bottom face 40 located adjacent to the reverse face 24 of the head part. When the connector is fully received in the bore 26 in the head part, the length of the contacting surfaces of the connector and the bore, measured along the axis of the bore, is from 19.75 to 22.25 mm. The widest point at which the connector is in contact with the bore is at the widest part of the connector part (that is at the bottom face 40). Accordingly, the ratio of the length of the contacting surfaces of the bore in the head part and the connector part when assembled, measured along the axis of the bore in the head part, to the diameter of the bore in the head part at the widest point at which it contacts the external surface of the connector part, is 1.23 (24.2:19.75) or 1.27 (28.3:22.25) in the two embodiments which are discussed.

The connector 30 has a bore 42 within it extending from the bottom face 40. The bore is tapered inwardly in a direction away from the bottom face of the connector. The bore is open at its opposite narrow end. The bore can be blind at its narrow end. A skirt 43 surrounds the bore at its open end on the bottom face 40.

The bore 42 in the connector is sized so that the spigot 14 on the stem is a snug fit within it.

Figure 5:
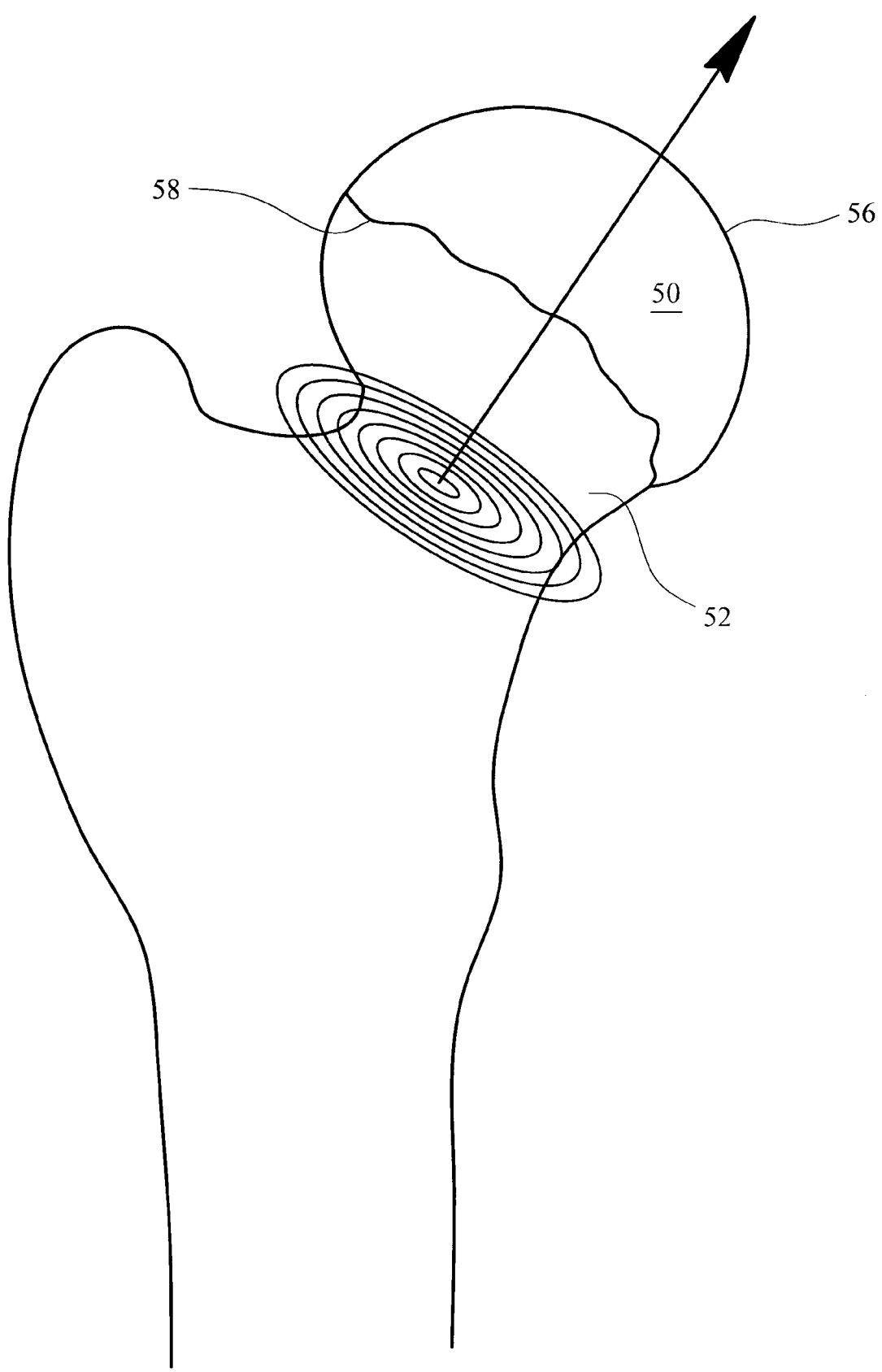
FIG. 5 is a view of the head of a femur to illustrate the offset of the bearing surface of the femoral head relative to the femoral neck.

FIG. 5 shows the head portion of a femur prior to any resection step in a procedure for replacement of a hip joint. The femur has a head part 50 and a neck 52 which extends between the head part and the femoral shaft 54. The outer bearing surface 56 of the head part is smooth, for articulation with a corresponding bearing surface within the acetabulum, and extends over the head part towards the femoral shaft to a boundary line 58. The bearing surface of the head part is defined by part of a sphere. The axis of the head part passes through the centre of the sphere, in a direction which is perpendicular to the plane which is defined by the boundary line 58.

The femoral neck 52 defines an axis which extends along its central core, between the femoral shaft and the head part.

The head part 50 of the femur can be offset relative to the femoral neck. A translational offset arises when there is a gap between the axis of the head part and the axis of the femoral neck. The size of the gap between the axes can be different from one patient to another, for example in the range 0 to 10 mm. The direction in which the axes are offset can vary, around the axis of the femoral neck.

Figure 6:
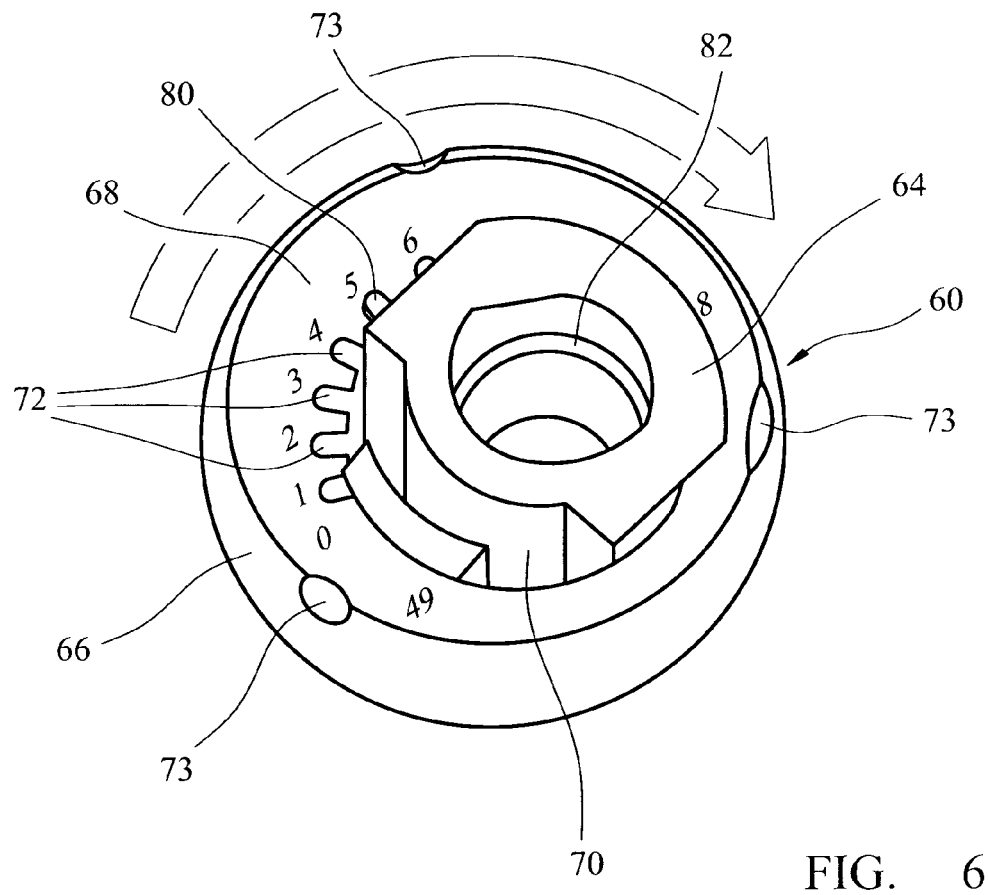
FIG. 6 is a view from below of a trial instrument which can be used to select the appropriate offset in an assembled femoral component.
Figure 7:
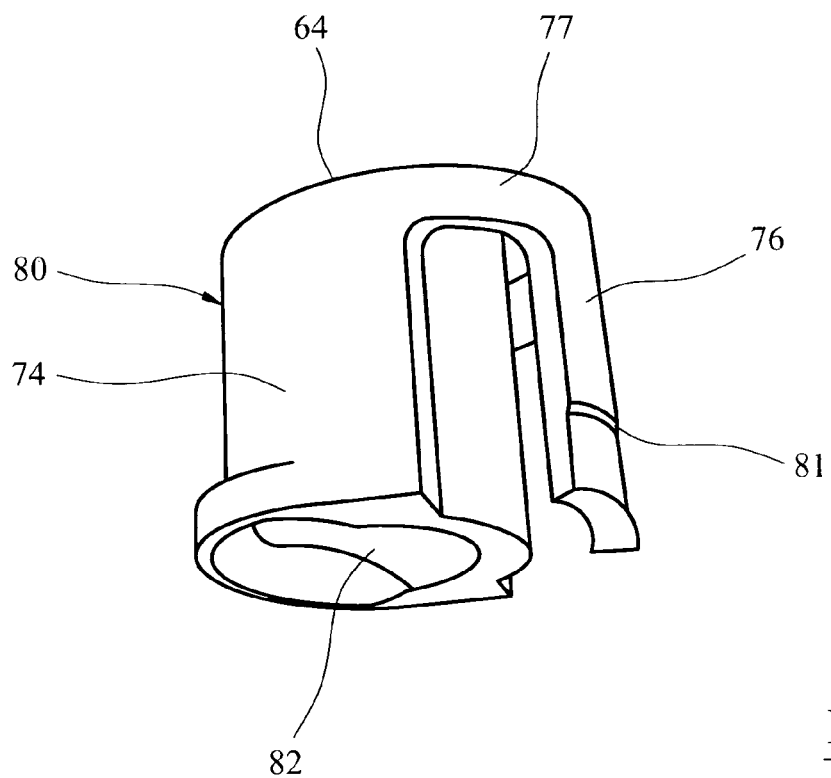
FIG. 7 is a side view of the trigger part of the trial instrument which is shown in FIG. 6.
Figure 8:
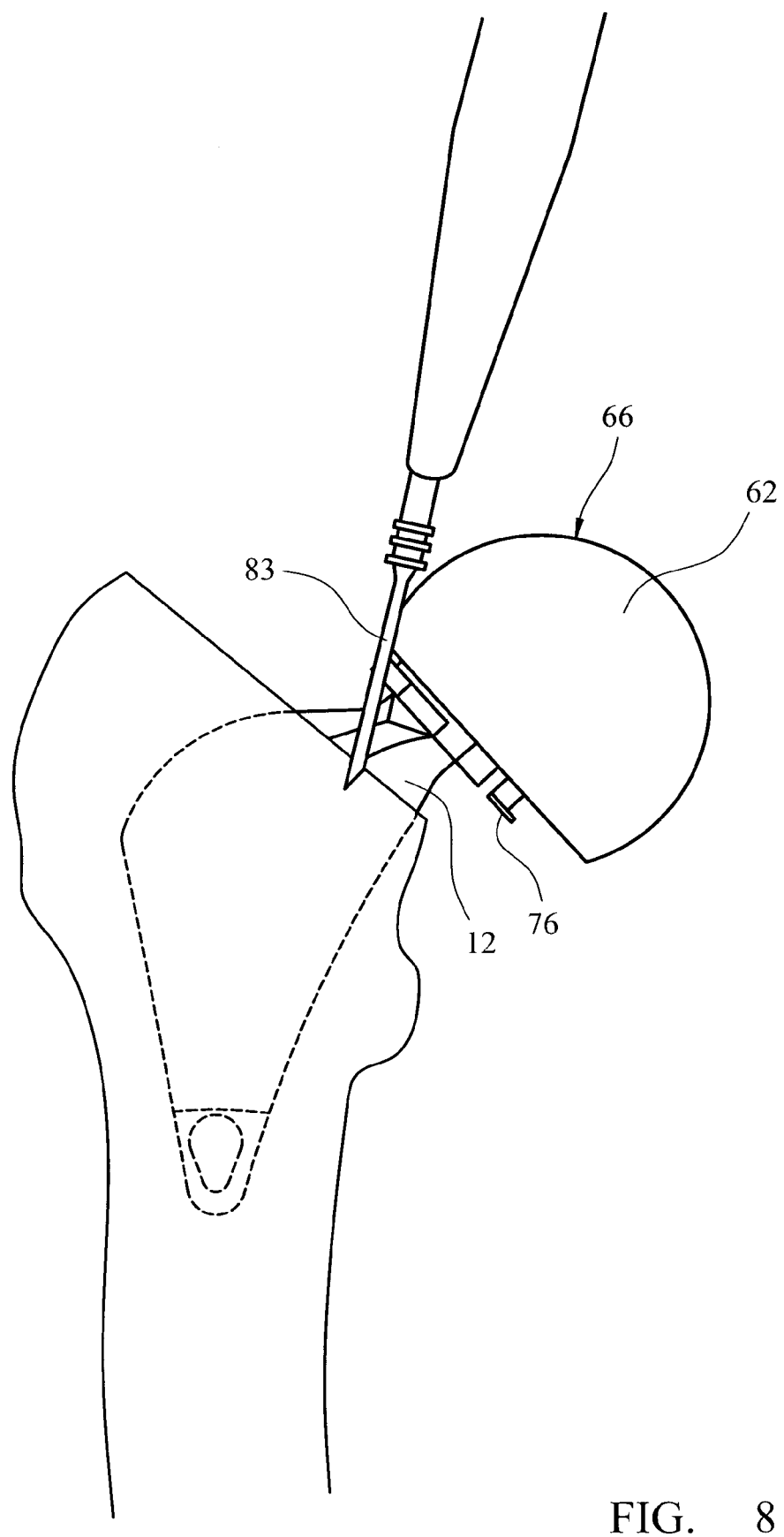
FIG. 8 is a side view of the head of the femur, with the trial instrument shown in FIG. 6 mounted on the stem part.

FIG. 6 shows an instrument 60 which can be used to trial the head part (with its connector) on an implanted stem part. The instrument comprises a trial head part 62 and a trial connector 64. The trial connector is shown in FIG. 7. The trial head part has a spherical outer surface 66 which corresponds to the bearing surface of the head part of the ultimate implant, and an opposite reverse face 68. The head part has a recess 70 within it extending inwardly from the reverse face towards the bearing surface. The recess is generally round when The recess has a plurality of grooves 72 in its side wall extending parallel to the axis of the recess. The trial head part can be formed from a metal such as a stainless steel or from a polymeric material.

The spherical outer surface 66 of the trial head part has three notches 73 at spaced apart points. The notches are distinguishable from one another, for example by means of distinguishing markings located adjacent to the notches.

The trial connector 64 is formed from a polymeric material. It comprises a body part 74 and a trigger 76 which is connected to the body part at one end 77. The material of the trigger 76, and of the body part when the trial connector is formed as a single piece) is sufficiently resilient that the trigger can be deformed inwardly towards the body part.

The body part has a rib 80 which is dimensioned so that it can fit into one of the grooves 72 in the side wall of the recess.

The trial head part and the trial connector have locking features so that the connector is retained within the recess 70 in the head part when the trigger is released, and can be removed from within the recess when the trigger is deformed towards the body part. The locking features can comprise an annular groove which extends around the recess, and a rib 81 on one or each of the body part and the trigger of the trial connector. When the rib is received in the groove, the trial connector is locked, against removal from the bore in the trial head part. When the trigger 76 is squeezed towards the body part 74, the trial connector is able to move transversely within the recess in the body part so that the rib can be withdrawn from the groove, allowing the trial connector to be withdrawn from within the recess.

The body part 74 of the trial connector has a bore 82 formed in it. The bore is tapered inwardly in a direction away from the bottom face of the connector. The bore is open at its opposite narrow end. The bore is blind at its narrow end. The bore 82 in the trial connector is sized so that the spigot 14 on the stern is a snug fit within it.

Figure 9:
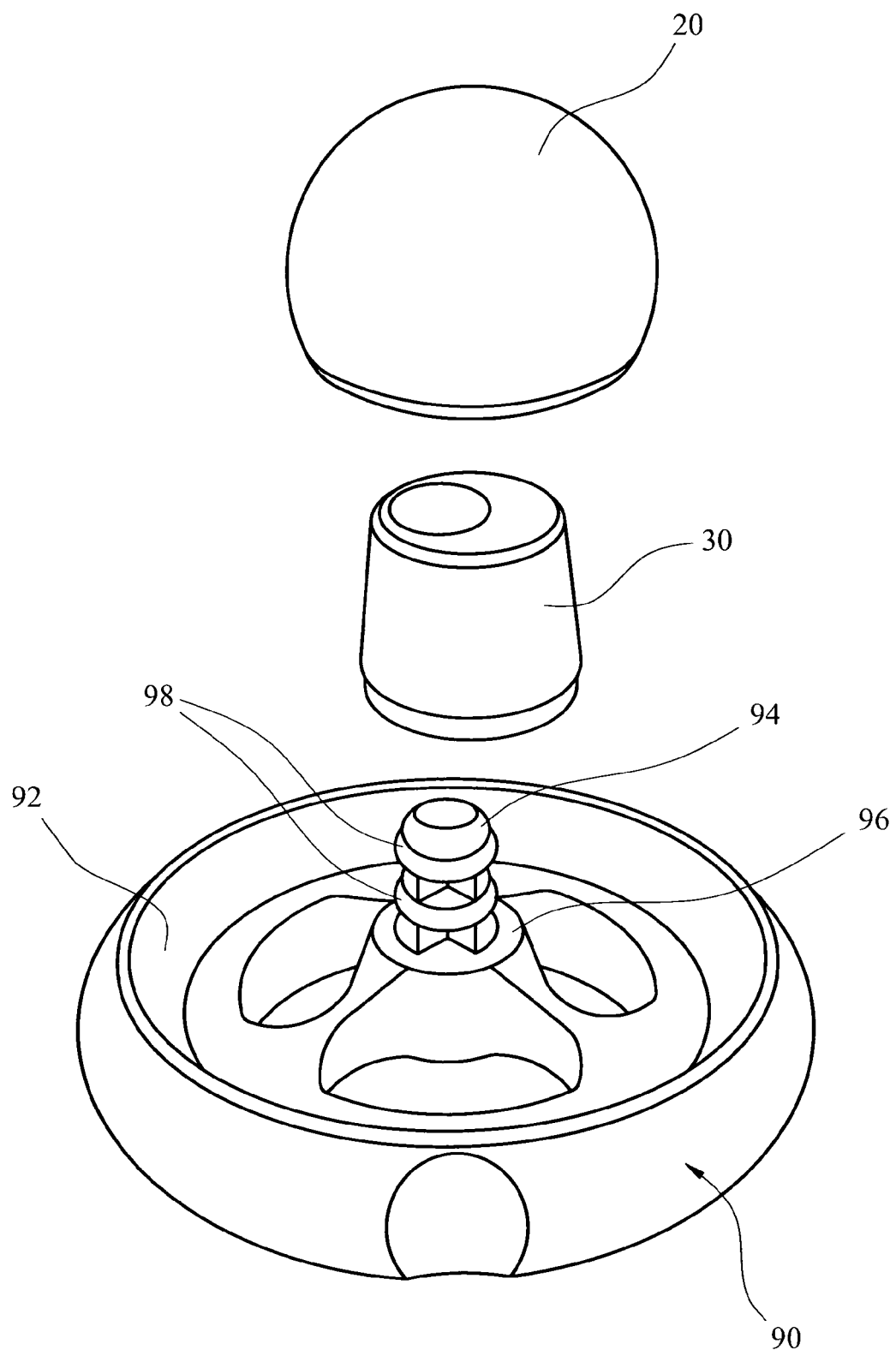
FIG. 9 is a side view of a tool which can be used to assemble the head part and the connector, shown in FIGS. 3 and 4 respectively.

FIG. 9 shows an assembly tool 90 which can be used in the assembly of the head part 20 of the femoral component and the connector 30. The tool comprises a base 92 having an upstanding spigot 94. The spigot has a collar 96 around, it, which presents an upwardly facing surface. A pair of compressible O-rings 98 are provided on the spigot, located in annular grooves therein. The sizes of the spigot and the O-rings are such that the O-rings are compressed on contact with the internal wall of the bore 42 in the connector 30 when the connector is seated on the tool with the bottom face of the skirt 13 in contact with the collar 96 on the tool. This can help to retain the connector on the spigot, by virtue of the friction forces between the O-rings and the internal surface of the bore in the connector.

The assembly tool 90 is made from stainless steel. It can have a ring of a rubber material located in a groove in its lower face such that it protrudes from the groove to engage the surface on which the tool is placed when in use.

Figure 10:
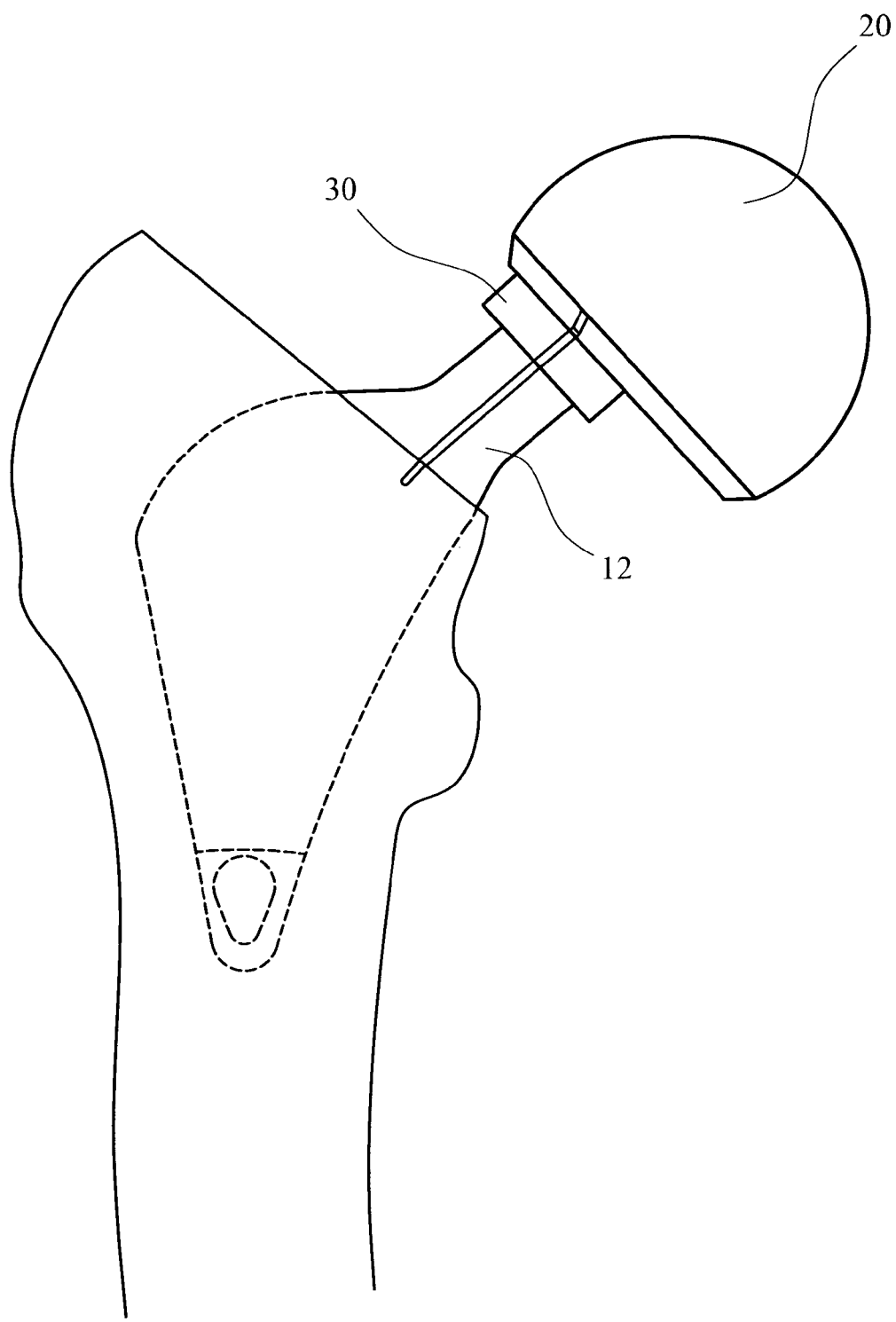
FIG. 10 is a view from one side of an assembled femoral component of a hip joint prosthesis according to the present invention.

FIG. 10 shows the femoral component of a hip joint prosthesis according to the present invention which has been assembled. The assembled femoral component comprises the head part 20, with the connector 30 located in the bore 26 therein. The spigot 14 on the stem part 12 of the femoral component is located in the bore 42 in the connector.

A procedure in which the invention can be implemented to provide a femoral component of a hip joint prosthesis can include the following steps.

Initial steps involve preparing the femur to receive the stem part. These steps are conventional, and include resection of the neck and head of the femur, and working on the intramedullary cavity in the femoral shaft so that it is appropriately dimensioned to receive the stem part.

Preparatory work on the patient might provide information as to the desired offset of the femoral head. The trial components described above with reference to FIGS. 4 to 6 can allow offsets to be assessed. Variations in the size of the gap between the axis of the head part and the axis of the femoral neck can be replicated by changing the angular relationship between the trial head part 62 and the trial connector 64, using the trigger to release the trial connector for movement in the recess in the trial head part. Variations in the direction in which the axes are offset can vary, around the axis of the femoral neck, can be replicated by rotating the trial components around the spigot 14 on the stem part 12.

Markings on the reverse face 68 of the trial head part 62 provide an indication of the size of the offset, which is then to be incorporated in the assembled head component.

A record of the angular orientation of the trial head part about the spigot 14 is made with reference to a selected one of the notches 73 on the spherical outer surface 66 of the trial head part, using a diathermy 83 to make a mark on bone tissue 84 immediately below the selected notch.

The size of the offset that is determined using the trial head part and the trial connector are reproduced in the head component with reference to the markings 28 on the reverse face 24 of the head part 20 (which are the counterparts to the grooves 72 in the side wall of the recess 70 in the reverse face 68 of the trial head part 62), and to a marking on the connector 30 (which is the counterpart to the rib 80 on the trial connector 64). The head part 20 and the connector 40 of the implant are assembled accordingly, and placed on the spigot 94 of the assembly tool 90. An impaction force is applied to the head part through an appropriate protector (such as a block of polyethylene which is configured to be a conforming fit on the bearing surface 22 of the head part 20). Application of the impaction force causes the connector to be forced downwardly on to the spigot 94 until the skirt 43 on the bottom face of the connector contacts the collar 96 on the tool, compressing the O-rings 98 on the spigot as necessary. When the skirt on the connector contacts the collar on the tool in this way, applied impaction force leads to securing of the connection between the head part 20 and the connector 40.

The assembled head component (comprising the head part 20 and the connector 40) is positioned on the spigot 14 on the stern part 12. The alignment of the head component on the stem part offset that is determined using the trial head part and the trial connector are reproduced in the head component with reference to a selected one of the markings 29 on the chamfer surface 28 which corresponds to the selected notch on the trial head part which was used previously to make a mark on the bone using the diathermy.

An impaction force is applied to the head component through an appropriate protector (such as a block of polyethylene which is configured to be a conforming fit on the bearing surface 22 of the head part 20) to cause the head component to become secured to the stem part. This is in line with existing assembly techniques for use with orthopaedic joint prostheses.

The invention claimed is:

1. An instrument for use in a joint replacement procedure, comprising:
   a head part which corresponds to the head of an orthopaedic joint component, wherein the head part has a bearing surface defined by a part of a sphere and a head axis defined by the bearing surface, and wherein the head part has a bore formed therein having a bore surface and a bore axis, the bore axis being located eccentrically relative to the head axis;
   a connector having an external surface, a connector axis defined by the external surface, and a connector feature having a connector feature axis, the connector feature adapted for connecting the head part to a corresponding connection feature on a stem part of the orthopaedic joint component which is intended for location in the intramedullary cavity of a bone, wherein the connector is at least partially disposable within the bore of the head part in one of a plurality of angular orientations, and wherein the connector comprises a body part and a trigger that is attached to the body part, the trigger being moveable relative to the body part between an unlocked position, where the connector can be moved relative to the head part between different ones of the plurality of angular orientations, and a locked position, where the trigger contacts the inner bore surface to restrain the connector from moving relative to the head part, the axis of the connection feature on the connector is located eccentrically relative to the connector axis, the connector axis being defined by the external surface that engages the bore in the head part when the connector and the head part are assembled.

2. The instrument of claim 1, wherein the trigger is biased resiliently away from the body.

3. The instrument of claim 1, wherein the connector and the head part present a cooperating rib and groove arrangement which, when the rib is engaged in the groove, resists angular adjustment of the connector within the bore of the head part.

4. The instrument of claim 3, wherein the rib and groove arrangement defines not more than ten angular positions of the connector relative to the head part.

5. The instrument of claim 1, wherein one of the connector and the head part has a lip formed thereon and the other of the connector and the head part has a groove formed therein, wherein the lip fits in the groove when the trigger is in the locked position, and can be withdrawn from the groove to allow the connector to be moved angularly relative to the head part.

6. The instrument of claim 5, wherein the lip is provided on the trigger.

7. An instrument as claimed in claim 1, further comprising a stem part that has a stem feature designed to connect to the connector feature.

8. The instrument of claim 1, wherein the head part or the connector or each of them is formed from a polymeric material.

9. The instrument of claim 7, wherein the connection feature on the connector comprises one of an inwardly tapered bore and a spigot, for cooperation with the stem feature, the stem feature comprising the other of an inwardly tapered bore and a spigot such that the spigot can be received in the bore to connect the stem part to the connector part.

10. The instrument of claim 1, wherein the head part has a perimeter and at least one marking on the perimeter.

11. The instrument of claim 10, wherein the head part has at least three markings on the perimeter, which are spaced apart approximately equally around the perimeter of the head part.

12. An assembly for use in a joint replacement procedure, comprising:
    the instrument of claim 1; and
    an orthopaedic joint component comprising: (i) a socket component; (ii) a head part having an axis and the shape of a truncated sphere with a convex bearing surface engageable and articulatable with the socket component and an opposite reverse face, the head part having a bore with a circular cross section, the bore having an end surface and being located eccentrically relative to the axis of the head part, wherein the bore extends into the head part from an opening on the reverse face and is inwardly tapered continuously from the opening towards the end surface; (iii) the stem part having a distal end and a head end, the distal end for fitting into a bone cavity; and (iv) a connector part having an external surface and a circular cross section which is tapered inwardly along the axis defined by the external surface so that the connector part is received snugly in the tapered bore in the head part.

13. The instrument of claim 1, wherein the trigger is connected at one end of the body part.

14. The instrument of claim 1, wherein, when the trigger is disposed within the bore of the head part, the trigger is translatable relative to the body part between the locked position and the unlocked position.

15. The instrument of claim 14, wherein the trigger is non-axially translatable relative to the body part.

16. The instrument of claim 1, wherein the body part has a body part bore centered on the axis of the connection feature, and wherein, when the trigger is disposed within the bore of the head part, the trigger is translatable relative to the body part bore between the locked position and the unlocked position.

* * * * *